United States Patent [19]

Vincent et al.

[11] Patent Number: 5,047,400

[45] Date of Patent: Sep. 10, 1991

[54] TRIPEPTIDE COMPOUNDS HAVING A NITROGENOUS POLYCYCLIC STRUCTURE

[75] Inventors: Michel Vincent, Bagneux; Georges Remond, Versailles; Bernard Portevin, Elancourt; Claude Cudennec, La Celle St-Cloud, all of France

[73] Assignee: Adir et Cie, Neuilly-sur-Seine, France

[21] Appl. No.: 207,710

[22] Filed: Jun. 16, 1988

[30] Foreign Application Priority Data

Jun. 16, 1987 [FR] France ................. 87 08350

[51] Int. Cl.$^5$ ................ A61K 31/40; C07D 221/02; C07D 217/00; C07D 209/46
[52] U.S. Cl. ................ 514/18; 546/112; 546/146; 546/147; 546/164; 546/165; 546/169; 546/175; 548/472; 548/515
[58] Field of Search ............ 546/146, 147, 112, 164, 546/165, 169, 175; 548/472, 515; 514/18

[56] References Cited

FOREIGN PATENT DOCUMENTS 190058 6/1986 European Pat. Off. .
2601957 1/1988 France .

*Primary Examiner*—Mary C. Lee
*Assistant Examiner*—Peter Davis
*Attorney, Agent, or Firm*—Gordon W. Hueschen

[57] ABSTRACT

The invention relates to the compounds of general formula:

$$R-\underset{Y}{\underset{|}{CH}}-\underset{X}{\underset{\|}{C}}-Lys-N\underset{\diagdown A \diagup}{\overset{\diagup\phantom{A}\diagdown}{\rule{0pt}{0pt}}}CH-CO-Arg\,OH \qquad (I)$$

in which:
X denotes either an oxygen atom, or two hydrogen atoms;
Y denotes either a hydrogen atom, or a hydroxyl group;
or Y denotes an amino group on condition that X denotes two hydrogen atoms;
R denotes a hydrogen atom, or a straight- or branched-chain alkyl group having 1 to 6 carbon atoms, optionally substituted with one or more hydroxy, amino, mercapto, methylthio or carboxy groups, or aryl groups such as phenyl, pyridyl or thienyl;

$$N\underset{\diagdown A \diagup}{\overset{\diagup\phantom{A}\diagdown}{\rule{0pt}{0pt}}}CH$$

denotes a polycyclic nitrogenous structure;
their enantiomers, epimers and diastereoisomers, as well as their addition salts with a pharmaceutically acceptable acid or base.

13 Claims, No Drawings

TRIPEPTIDE COMPOUNDS HAVING A NITROGENOUS POLYCYCLIC STRUCTURE

The present invention relates to new tripeptides, the preparation and pharmaceutical compositions containing them.

Many natural or synthetic peptides which modify the biological response are known, and in particular tuftsin, a natural tetrapeptide of formula Thr-Lys-Pro-Arg.

A tuftsin analog in which threonine is replaced by an oxazolidinone-carboxy radical has been described by Y. STABINSKY et al. (Int. J. Peptide, Protein Research, 1978; 12; 130-138). However, this compound retains only about half the activity of tuftsin.

European Patent Application No. 0,190,058 describes tuftsin analogs in which proline is replaced by a polycyclic nitrogenous structure.

However, all these compounds, according to recent work (V. A. NAJJAR; Annals of the New York Academy of Science; Volume 419—Antineoplastic, immunogenic and other effects of the tetrapeptide tuftsin, New York Academy of Sciences, New York—1983), possess the disadvantage of suffering the action of a specific aminopeptidase which cleaves tuftsin or its homologs:
on the one hand to a threonyl radical,
and on the other hand to a tripeptide (Lys-Pro-Arg, in the case of tuftsin) which is an inhibitor of the activity of the original tetrapeptide.

This aminopeptidase hence renders tuftsin and its derivatives inactive fairly rapidly.

However, this aminopeptidase can act only on compounds simultaneously possessing an amino group in the α-position with respect to the carbonyl group of the peptide bond involving the amino group of lysine, that is to say the following structure:

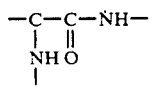
(a)

The Applicant has now discovered new compounds whose level of activity is greater than that of tuftsin but which no longer possess the tetrapeptide structure, and are hence devoid of the structure (a); in effect, the threonine has been replaced by a structure which is not an α-amino acid, which is grafted onto the lysyl residue. These new tripeptides hence offer the specially advantageous feature of possessing a high level of activity while being insensitive to the action of the aminopeptidase, and consequently of possessing an activity that is less transitory and hence more compatible with a therapeutic use; this results, in addition, in possibilities of use in therapy at a lower dosage, with more widely spaced successive administrations.

More specifically, the invention relates to compounds of general formula:

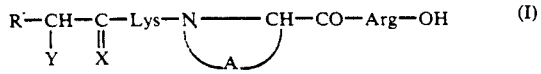

in which:
X denotes either an oxygen atom, or two hydrogen atoms;
Y denotes either a hydrogen atom, or a hydroxyl group;
or
Y denotes an amino group on condition that X denotes two hydrogen atoms;
R denotes a hydrogen atom, or a straight- or branched-chain alkyl group having 1 to 6 carbon atoms, optionally substituted with one or more hydroxy, amino, mercapto, methylthio or carboxy groups, or aryl groups such as phenyl, pyridyl or thienyl;
Lys and Arg denote, respectively, lysyl and arginyl residues engaged in peptide bonds,

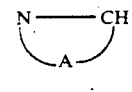

denotes
* a bicyclic structure of formula

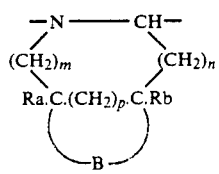

where
m equals 1 or zero,
n and p denote zero, 1 or 2,
Ra and Rb denote a hydrogen atom, or can form together a direct bond when p=0,
B denotes:
* an alkylene chain $(CH_2)_q$, where q equals 2, 3 or 4, or
* an unsaturated structure $(-CH=CH-)_2$ when p=0 and Ra and Rb together form a bond, with the proviso that the sum m, n, p and q is an integer between 3 and 6, or 1,2,3,4-tetrahydro-beta-carboline;
their enantiomers, epimers and diastereoisomers, as well as their addition salts with a pharmaceutically acceptable acid or base.

At present, among the compounds of the formula (I), those are preferred in which the cyclic structure

denotes indoline, isoindoline, tetrahydroquinoline, tetrahydroisoquinoline, perhydroindole, perhydroisoindole, perhydroquinoline, perhydroisoquinoline, perhydrocyclopenta[b]-pyrrole, 2-azabicyclo[2.2.2]octane, 2-azabicyclo[2.2.1]-heptane or 1,2,3,4-tetrahydro-beta-carboline.

Among the acids which may be added to the compounds of the formula (I) to form an addition salt, there may be mentioned, by way of example, hydrochloric, sulfuric, phosphoric, tartaric, malic, maleic, fumaric, oxalic, methanesulphonic, ethanesulphonic, camphoric and citric acids, and the like.

As bases capable of salifying the compounds of formula (I), there may be used sodium, potassium, calcium or aluminium hydroxides, alkali metal or alkaline earth metal carbonates or organic bases such as triethylamine, benzylamine, diethanolamine, tert-butylamine, dicyclohexylamine and arginine, and the like.

The invention also encompasses the process for producing the compounds of the formula (I), wherein a compound of formula (II):

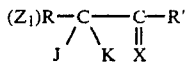

in which:
* R and X have the same meaning as in the formula (I),
* R' denotes:
  either a hydrogen atom or a hydroxyl group when X denotes an oxygen atom,
  or a halogen atom, preferably a bromine atom, on condition that, in this case, X denotes two hydrogen atoms,
* J denotes a hydrogen atom or a hydroxyl group, on condition that K denotes a hydrogen atom, or alternatively J denotes a benzyloxycarbonylamino group on the dual condition that K and R' each denote a hydrogen atom, or alternatively J and K together denote an oxygen atom, on condition that X denotes two hydrogen atoms,
* $(Z_1)$ denotes a group which protects the possible amino substituents of the radical R, and especially a benzyloxycarbonyl group, is condensed with a compound of formula (III):

Lys (Z)—OtBu    (III)

in which
(Z) denotes a group which protects the ω-amino substituent of the lysine, and especially a benzyloxycarbonyl group, and tBu denotes a group which protects the carboxyl group, and especially a tert-butyl radical, in the presence of:
a reducing agent such as, for example, a mixed alkali metal hydride such as, for example, an alkali metal borohydride or alternatively an alkali metal cyanoborohydride when R' denotes a hydrogen atom,
a customary peptide coupling agent such as dicyclohexylcarbodiimide in the presence of hydroxybenzotriazole when R' denotes a hydroxyl group,
a basic agent such as, for example, an alkali metal salt such as, for example, an alkali metal carbonate such as sodium carbonate when R' denotes a halogen atom, to obtain a derivative of formula (IV):

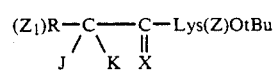

in which R and X have the same meaning as in the formula (I), J, K and $(Z_1)$ the same meaning as in formula (II) and (Z) and tBu the same meaning as in the formula (III), which is deprotected in acid medium in respect of the carboxylic acid group of the lysine to a compound of formula (V):

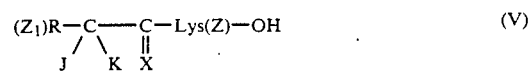

in which R and X have the same meaning as in the formula (I), J, K and $(Z_1)$ the same meaning as in the formula (II) and (Z) the same meaning as in the formula (III), which is then condensed with a compound of the formula (VI):

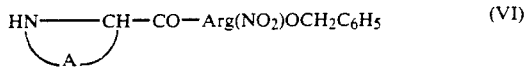

in which A has, with the carbon and nitrogen atoms to which it is attached, the same meaning as in the formula (I) which compound is itself obtained by condensation of a compound of the formula (VII):

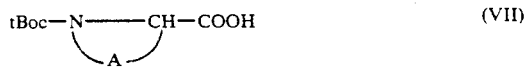

in which A has, with the carbon and nitrogen atoms to which it is attached, the same meaning as in the formula (I) and tBoc denotes a tert-butoxycarbonyl radical, the latter derivative being obtained as described in European Patent Application No. 0,190,058, with benzyl $N^\omega$-nitroarginate (H—Arg($NO_2$)—$OCH_2C_6H_5$) to obtain a derivative of formula (VIII):

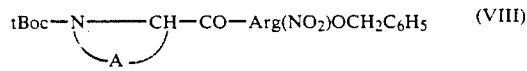

in which A, with the carbon and nitrogen atoms to which it is attached, has the same meaning as in the formula (I), which is then deprotected with trifluoroacetic acid according to the method described by B. GUTTE and K. B. MERRIFIELD (J. Am. Chem. Soc. 1969, 91, 501) to the compound of formula (VI), the condensation of the derivative of formula (V) with the compound of formula (VI) enabling a compound of formula (IX):

to be obtained, in which formula A, with the carbon and nitrogen atoms to which it is attached, R and X have the same meaning as in formula (I), J, K and $(Z_1)$ the same meaning as in formula (II) and (Z) the same meaning as in the formula (III), which, when J and K together denote an oxygen atom, is subjected to the action of a mixed alkali metal hydride such as sodium borohydride, it being possible for the compound thereby obtained, if so desired, to be separated into its isomers by a classical separation technique such as chromatography on a silica column, to obtain a compound of general formula (IXa), a special case of the derivatives of formula (IX) in which A, with the carbon and nitrogen atoms to which it is attached, R, X, $(Z_1)$ and (Z) have the same meaning as in the formula (IX), J denotes a hydroxyl group and K denotes a hydrogen atom, which compound of formula (IX) or (IXa) is deprotected by hydrogenolysis in an acidic polar solvent in the presence of a hydrogenation catalyst to yield a derivative of formula (I), which can, if so desired:
either be salified with a pharmaceutically acceptable acid or base, or be separated into its isomers and then, if necessary, salified with a pharmaceutically acceptable acid or base.

The compounds of formula (IX) and (IXa) are new and form part of the invention in the same manner as the derivatives of formula (I), of which they constitute the synthesis intermediates.

The compounds of formula (I) are endowed with advantageous pharmacological properties.

In particular, the main properties of the compounds of European Patent Application No. 0,190,058 are also found in these compounds, at a higher or at least comparable level.

More particularly, these compounds increase the activity of "natural killer" NK cells. When administered to mice bearing an melanoma, they substantially inhibit the growth of this melanoma. They bring about a promotion of the immune defenses in animals infected with pathogenic bacterial strains.

These activities are linked to the immunomodulatory properties of the compounds of the invention, which find their application, in animal or human therapy, in the treatment of cancers, conditions of viral, bacterial or fungal origin, autoimmune diseases such as lupus erythematosus or rheumatoid arthritis, and more generally in diseases resulting from a decrease or disturbance of the natural immune responses of the animal or human body.

In addition, the novel structure possessed by the compounds of the present invention renders them insensitive to the action of a specific aminopeptidase, as stated above. This makes their activity less transitory than that of the compounds of the prior art, and hence distinctly more compatible with a therapeutic use, making possible, in particular, a lower dosage as well as successive administrations that are spaced over wider time intervals.

The subject of the invention is also pharmaceutical compositions containing at least one compound of general formula (I), or one of its addition salts with a pharmaceutically acceptable acid or base, alone or in combination with one or more pharmaceutically acceptable, non-toxic inert vehicles or excipients.

Among the pharmaceutical compositions according to the invention, there may be mentioned, more especially, those which are suitable for oral, parenteral, peror transcutaneous, nasal, rectal, perlingual, ocular or respiratory administration, and in particular the injectable preparations, aerosols, eye or nose drops, tablets, sublingual tablets, sublingual preparations, gelatin capsules, capsules, pills, suppositories, creams, ointments, skin gels, and the like.

The appropriate dosage varies according to the patient's age and weight, the administration route, the nature of the therapeutic indication and possible associated treatments, and ranges between 1 microgram and 1 gram per dose or per application.

The examples which follow illustrate the invention, and in no way limit the latter.

The starting substances are known in the literature.

The stated melting points are measured according to the micro-Kofler technique.

EXAMPLE 1

(2S, 3R) AHPA-(S) LYS-(S) PHI-(S) Arg OH

AHPA-OH: 2-Hydroxy-3-amino-4-phenylbutanoic acid
(S)PHI-OH: (2S, 3aS, 7aS)-perhydro-2-indolecarboxylic acid

STAGE A tBoc (S) PHI-(S) Arg $(NO_2)OCH_2 C_6H_5$

Using the method of W. KONIG and R. GEIGER (Ber., 1970, 103, 788), 0.004 mole of tBoc (S) PHI-OH, described in European Patent Application No. 0,190,058, is coupled with 0.004 mole of benzyl (S)-$N^\omega$-nitroarginate, using anhydrous dimethylformamide as solvent.

tBoc (S) PHI-(S) Arg $(NO_2)$ $OCH_2C_6H_5$ is obtained, and used without further treatment in the following stage.

STAGE B (S) PHI-(S) Arg $(NO_2)$ $OCH_2 C_6H_5$

Using the method of deprotection with trifluoroacetic acid in anhydrous methylene chloride, described by B. GUTTE and R. B. MERRIFIELD (J. Am. Chem. Soc., 1969, 91, 501), (S) PHI-(S) Arg $(NO_2)$ $OCH_2C_6H_5$ is obtained quantitatively in the form of a trifluoroacetate from tBoc (S) PHI-(S) Arg $(NO_2)$ $OCH_2C_6H_5$ prepared in the preceding stage.

STAGE C (Z)-(2S, 3R) AHPA-(S) Lys (Z) OtBu (Z) (2S, 3R) AHPA, described by R. NISHIZAWA et al. (J. Med. Chem., 1977, 20, 4, 510–515) is condensed with the derivative (S) Lys (Z)-OtBu according to the method of W. KONIG and GEIGER (Chem. Ber., 1970, 103, 788) to obtain (Z) (2S, 3R) AHPA-(S) Lys (Z) OtBu which is used without further treatment in the following stage.

STAGE D (Z)-(2S, 3R) AHPA-(S) Lys (Z)-OH

The terminal carboxyl group of (Z)-(2S, 3R)-AHPA - (S) Lys (Z) OtBu is deprotected with trifluoroacetic acid. After the product is taken to dryness and solidified in ethyl ether, (Z)-(2S, 3R) AHPA-(S)-Lys (Z)-OH is obtained.

STAGE E (Z)-(2S, 3R) AHPA-(S) Lys (Z)-(S) PHI-(S) Arg $(NO_2)$ $OCH_2 C_6H_5$ (Z)-(2S, 3R) AHPA-(S) Lys (Z)-OH obtained in the preceding stage is coupled according to the method used in Stage A with (S) PHI-(S) Arg $(NO_2$ $OCH_2$ $C_6H_5$, which was itself obtained in Stage B.

The (Z)-(2S, 3R) AHPA-(S) Lys (Z)-(S) PHI-(S) Arg $(NO_2)$ $OCH_2 C_6H_5$ thereby obtained is purified by chromatography on silica gel (eluant: methylene chloride/methanol 95:5; Rf: 0.15).

STAGE F (2S, 3R) AHPA-(S) Lys-(S) PHI-(S) Arg OH 650 mg of (Z) (2S, 3R) AHPA-(S) Lys (Z)-(S) PHI-(S) Arg $(NO_2)$ $OCH_2$ $C_6H_5$, obtained in the preceding stage, are dissolved in 100 cm³ of acetic acid, 200 mg of palladinized charcoal (10% palladium) are added and the mixture is hydrogenated for 20 hours under a pressure of 3 kg/cm². After the catalyst is filtered off and the acetic acid evaporated off, the residue is dissolved in 50 cm³ of water and the solution filtered and the lyophilized. (2S, 3R) AHPA-(S) Lys-(S) PHI-(S) Arg OH (360 mg) is obtained in the form of a diacetate.

Mass spectrometry: (DCI spectrum $(NH_3)$)

M/Z: 571: $[M + H - H_2O - HN= .=NH]^-$

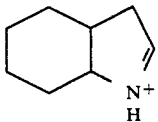

122: $C_6H_5-CH_2-CH_2-NH_3^+$
115: $[Arg + H-H_2O-HN=.=NH]^+$

EXAMPLE 2

(2R, 3R) AHPA-(S) Lys-(S) PHI-(S) Arg OH

By the procedure used in Example 1, starting with (Z) (2R, 3R) AHPA (J. Med. Chem. 1977, 20, 510–515), the following are obtained successively:
(Z) (2R, 3R) AHPA-(S) Lys (Z)-OtBu
(Z) (2R, 3R) AHPA-(S) Lys (Z)-OH
(Z) (2R, 3R) AHPA-(S) Lys (Z)-(S) PHI-(S) Arg (NO$_2$) OCH$_2$C$_6$H$_5$
(2R, 3R) AHPA-(S) Lys-(S) PHI-(S) Arg OH in the form of a diacetate.

Mass spectrometry: (DCI spectrum (NH$_3$))

M/Z: 571: $[M + H-H_2O-HN=.=NH]^+$

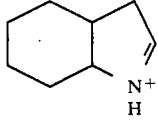

115: $[Arg + H-H_2O-HN=.=NH]^+$

EXAMPLE 3

(2S, 3S) AHPA-(S) Lys-(S) PHI-(S) Arg OH

By the procedure used in Example 1, starting with (Z)-(2S, 3S) AHPA (J. Med. Chem. 1977, 20, 510–515), the following are obtained successively:
(Z) (2S, 3S) AHPA-(S) Lys (Z)-OtBu
(Z) (2S, 3S) AHPA-(S) Lys (Z)-OH
(Z) (2S, 3S) AHPA-(S) Lys (Z)-(S) PHI-(S) Arg (NO$_2$) OCH$_2$C$_6$H$_5$
(2S, 3S) AHPA-(S) Lys-(S) PHI-(S) Arg OH in the form of a diacetate.

Mass spectrometry: (DCI spectrum (NH$_3$))

M/Z: 613: $[M + H-H_2O]^+$
589: $[M + H-HN-.-NH]^+$
571: $[M + H-H_2O-HN=.=NH]^+$

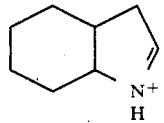

EXAMPLE 4

(2R, 3S) AHPA-(S) Lys-(S) PHI-(S) Arg OH

By the procedure used in Example 1, starting with (Z)-(2R, 3S) AHPA (J. Med. Chem. 1977, 20, 4, 510–515), the following are obtained successively:
(Z) (2R, 3S) AHPA-(S) Lys (Z)-tBu
(Z) (2R, 3S) AHPA-(S) Lys (Z)-OH
(Z) (2R, 3S) AHPA-(S) Lys (Z)-(S) PHI-(S) Arg (NO$_2$)-OCH$_2$C$_6$H$_5$
(2R, 3S) AHPA-(S) Lys-(S) PHI-(S) Arg OH in the form of a diacetate.

Mass spectrometry: (DCI spectrum (NH$_3$))

M/Z: 571: $[M + H-H_2O-HN=.=NH]^+$

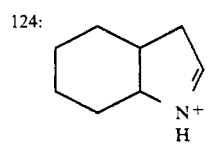

115: $[Arg + H-H_2O-HN=.=NH]^+$

EXAMPLE 5

(2S, 3R) AHPA-(S) Lys-(S) ABO-(S) Arg OH

ABO-OH: 2-azabicyclo[2.2.2]octane-3-carboxlic acid

By the procedure used in Example 1, and replacing tBoc (S) PHI-OH in Stage A by tBoc (S) ABO-OH described in European Patent Application No. 0,190,058, the following are obtained successively:

STAGE A tBoc (S) ABO-(S) Arg (NO$_2$)-OCH$_2$C$_6$H$_5$

STAGE B (S) ABO-(S) Arg (NO$_2$)-OCH$_2$C$_6$H$_5$ which is condensed with (Z)-(2S, 3R) AHPA-(S) Lys (Z)-OH, obtained in Example 1, to obtain successively:
(Z) (2S, 3R) AHPA-(S) Lys (Z)-(S) ABO-(S) Arg (NO$_2$)-OCH$_2$ C$_6$H$_5$ (2S, 3R) AHPA-(S) Lys-(S) ABO-(S) Arg OH in the form of a diacetate.

Mass spectrometry: (DCI spectrum: (NH$_3$))

Mass spectrometry: (DCI spectrum: (NH$_3$))
M/Z: 575: $[M + H = HN = . = NH]^+$
557: $[M + H - H_2O - HN = . = NH]^+$
120: $[C_6H_5 - CH_2 - CH = NH_2]^+$

EXAMPLES 6 AND 7

N-[(2S, 3R)-2-Hydroxy-3-aminobutyryl]-(S) Lys-(S) ABO-(S) Arg-OH (α isomer) and N-[(2R, 3R)-2-Hydroxy-3-aminobutyryl]-(S) Lys-(S) ABO-(S) Arg-OH (β isomer)

STAGE A

By replacing (Z)-(2S, 3R) AHPA in Example 1, Stages A and B, by (2RS, 3R)-2-hydroxy-3-[(Z)-amino]-butyric acid described by R. NISHIZAWA and T. SAINO (J. Med. Chem. 1977, 20, 4, 510–515), the following are obtained successively:

N-{(2RS, 3R)-2-Hydroxy-3-[(Z)-amino]butyryl}-(S) Lys (Z)-OtBu and then N-{(2RS, 3R)-2-Hydroxy-3-[(Z)-amino]butyryl}-(S) Lys (Z)-OH

STAGE B

N-{(2S, b 3R)-2-Hydroxy-3-[(Z)-amino]butyryl}-(S) Lys (Z)-(S) ABO-(S) Arg (NO₂)-OCH₂C₆H₅ and N-{(2R, 3R)-2-Hydroxy-3-[(Z)-amino]butyryl}-(S) Lys (Z)-(S) ABO-(S) Arg (NO₂)-OCH₂C₆H₅

N-{(2RS, 3R)-2-Hydroxy-3-[(Z)-amino]butyryl} (S) Lys (Z)-OH, obtained in the preceding stage, is coupled according to the technique used in Example 1, Stage E, with (S) ABO-(S) Arg (NO₂)-OCH₂C₆H₅ (see Example 5) to give N-{(2RS, 3R)-2-hydroxy-3-[(Z)-amino]-butyryl}-(S) Lys (Z)-(S) ABO-(S) Arg (NO₂)-OCH₂C₆H₅ The two isomers are separated by chromatography on silica gel, using a methylene chloride/methanol (96 : 4) mix-ture as eluant.

| Thin layer chromatography: | support: silica Si 60 F 254. |
| --- | --- |
| | solvent: ethyl acetate. |
| | α isomer Rf: 0.19 |
| | β isomer Rf: 0.12 |

STAGE C

N-[(2S, 3R)-2-Hydroxy-3-aminobutyryl]-(S) Lys-(S) ABO-(S) Arg-OH and N-[(2R, 3R)-2-Hydroxy-3-aminobutyryl]-(S) Lys (S) ABO-(S) Arg-OH Each of the isomers obtained in the preceding stage is treated according to the technique used in Example 1, Stage F, to obtain:

EXAMPLE 6

N-[(2S, 3R)-2-Hydroxy-3-aminobutyryl]-(S) Lys-(S) ABO-(S) Arg-OH, lyophilized in the form of a diacetate.

EXAMPLE 7

N-[(2R, 3R)-2-Hydroxy-3-aminobutyryl]-(S) Lys-(S) ABO-(S) Arg-OH, lyophilized in the form of a diacetate.
For both isomers:

| thin layer chromatograohy: | support: silica Si 60 F 254 |
| --- | --- |
| | solvent: |
| | ethyl acetate: 20 |
| | pyridine: 20 |
| | water: 15 |
| | acetic acid: 5 |
| | Rf.: 0.17 |

Mass spectrometry: [FAB]+

| M/Z: | 563: [M + Na]+ |
| --- | --- |
| | 541: [M + H]+ |
| 110: | |

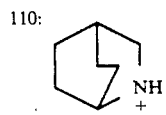

(The FAB+ mass spectra of the 2 isomers are identical)

EXAMPLE 8

(3S, 4S) Sta-(S) Lys-(S) ABO-(S) Arg OH

Sta = statine = 3-hydroxy-4-amino-6-methylheptanoic acid

STAGE A (Z)-(3S, 4S) Sta (3S, 4S)-Statine, prepared according to the method of D. H. RICH, E. T. SUN and A. S. BOPARAI (J.O.C., 1978, 43, 18, 3624–3626) is converted to (Z)-(3S, 4S)-statine using the technique of M. BERGMANN and L. ZERVAS (Ber. 1932, 65, 1192).

STAGE B

By replacing (2RS, 3R)-2-hydroxy-3-[(Z)-amino]-butyric acid in Examples 6 and 7 by (Z)-(3S, 4S) Sta, the following are obtained successively:
(Z)-(3S, 4S) Sta-(S) Lys (Z) OtBu
(Z)-(3S, 4S) Sta-(S) Lys (Z) OH
(Z)-(3S, 4S) Sta-(S) Lys (Z)-(S) ABO-(S) Arg (NO₂) OCH₂C₆H₅
(3S, 4S) Sta-(S) Lys-(S) ABO-(S) Arg OH
in the form of a diacetate.

Mass spectrometry: (DCI spectrum (NH₃))

| M/Z: | 537: [M + H−H₂O−HN=.=NH]⁻ |
| --- | --- |
| 110: | |

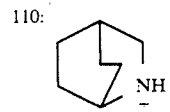

EXAMPLE 9: (R,S) GABOB-(S) Lys-(S) ABO-(S) Arg OH

GABOB: 3-Hydroxy-4-aminobutyric acid

By replacing (3S, 4S)-statine in Example 8 by GABOB, the following are obtained successively:
(Z)-(R, S) GABOB
(Z)-(R, S) GABOB-(S) Lys (Z) OtBu
(Z)-(R, S) GABOB-(S) Lys (Z) OH
(Z)-(R, S) GABOB-(S) Lys (Z)-(S) ABO-(S) Arg (NO₂) OCH₂C₆H₅
(R, S) GABOB-(S) Lys-(S) ABO-(S) Arg OH
which is lyophilized in the form of a diacetate.

Mass spectrometry: FAB+ spectrum

| M/Z: | 563: [M + Na]+ |
| --- | --- |
| | 541: [M + H]+ |
| 115: | |

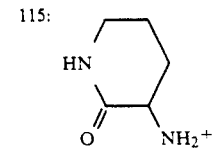

110:

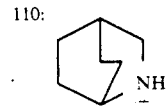

EXAMPLE 10

[(S)-3-Phenyl-2-aminopropyl]-(S) Lys-(S)-ABO-(S) Arg-OH

STAGE A: {(S)-3-Phenyl-2-[(Z)-amino]propyl} (S) Lys (Z)-OtBu (Z)-(S)-Phenylalaninal, obtained according to the method of R. NISHIZAWA and T. SAINO (J. Med. Chem. 1977, 20, 510–515), is subjected to reductive amination in the presence of sodium cyanoborohydride with (S) Lys (Z)-OtBu according to the technique of J. Martinez (J.Med. Chem. 1985, 28, 1874-1879). {(S)-3-Phenyl-2-[(Z)amino]propyl}-(S) Lys (Z)-OtBu, purified by chromatography on silica gel (eluant: methylene chloride/ethanol 95:5), is obtained in a 74% yield.

Spectral characteristics:
Infrared:
vs NH : 3320 cm$^{-1}$
vs CO : 1720 cm$^{-1}$

STAGE B

{(S)-3-Phenyl-2-[(Z)-amino]propyl} (S) Lys (Z)-OH 15 g of {(S)-3-phenyl-2-[(Z)-amino]propyl} (S) Lys (Z)-OH, obtained in the preceding stage, are subjected for 18 hours at room temperature to the action of a 2N solution of hydrochloric acid in ethyl acetate. After the mixture is taken to dryness and the residue is taken up in ether, followed by filtration and washing with ethyl acetate, {(S)-3-phenyl-2-[(Z)-amino]propyl} S) Lys (Z)-OH is recovered in a 66% yield in the form of a hydrochloride.

Spectral characteristics:
Infrared: v(C=O) : 1730 and 1680 cm$^{-1}$

STAGE C: {(S)-3-Phenyl-2-[(Z)-amino]propyl}(S) Lys-(S) ABO-(S) Arg OH

By replacing (2S, 3R) AHPA-(S) Lys (Z)-OH in Example 5 by {(S)-3-phenyl-2-[(Z)-amino]propyl}-(S) Lys (Z)-OH, obtained in the preceding stage, the following are obtained successively:

* {(S)-3-Phenyl-2-[(Z)-amino]propyl}-(S) Lys (Z)-(S) ABO-(S) Arg. (NO$_2$) OCH$_2$-C$_6$H$_5$
* [(S)-3-Phenyl-2-aminopropyl]-(S) Lys-(S)ABO-(S) Arg OH, which is lyophilized in the form of a triacetate.

Spectral characteristics:
Mass spectrometry:
FAB$^+$ spectrum [M+H]$^+$ M/Z : 573.
FAB$^-$ spectrum [M-H]$^-$ M/Z : 571.

EXAMPLE 11

[(2S, 3S)-2-Hydroxy-3-amino-4-phenylbutyl]-(S) Lys-(S) ABO-(S) Arg-OH (α isomer)

and

EXAMPLE 12

[(2R, 3S)-2-Hydroxy-3-amino-4-phenylbutyl]-(S) Lys-(S) ABO-(S) Arg-OH (β isomer)

STAGE A (S)-3-Benzyloxycarbonylamino-4-phenyl-2-oxo-1-bromobutane

The mixed anhydride between (Z)-(S)-phenylalanine and isobutyl chloroformate is prepared according to the technique described by H. BODANSKY and A. BODANSKY ("The practice of peptide synthesis", p 109 Springer Verlag (1984)); a solution of 25 mmol of this mixed anhydride in 50 cm$^3$ of THF is thereby obtained.

An ethereal solution of diazomethane (1.8 g in 250 cm$^3$) is added in the course of 1 hour to this solution, cooled to 0° C., the mixture is stirred for 3 h 30 min at 20° C. and the excess diazomethane is then driven off with a stream of nitrogen. The diazo ketone obtained (thin layer chromatography: silica Si 60 F 254 support, toluene/ethyl acetate 75:25 solvent, Rf.: 0.25) is converted to (S)-3-benzyloxycarbonylamino-4-phenyl-2-oxo-1-bromobutane according to the technique of I. H. HALL and L. J. LOEFFLER (J. Med. Chem. 1980, 23, 275–278) in a 68% yield. Thin layer chromatography: silica Si 60 F 254 support, toluene/ethyl acetate 75:25 solvent, Rf.: 0.45.

Spectral characteristics:
vs NH : 3320 cm$^{-1}$
vs CO (carbamate): 1740 cm$^{-1}$
vs CO (ketone) : 1690 cm$^{-1}$

STAGE B

N-[(S)-3-Benzyloxycarbonylamino-4-phenyl-2-oxobutyl]-(S) Lys (Z) OH 20 mmol of (S)-3-benzyloxycarbonylamino-4-phenyl2-oxo-1-bromobutane, obtained in the preceding stage, are dissolved in a mixture of 90 cm$^3$ of tetrahydrofuran and 10 cm$^3$ of dimethylformamide. 2 mmol of (commercial) (S) Lys (Z) OtBu trifluoroacetate and 4 mmol of sodium carbonate are added, and the mixture is then brought for 3 hours to reflux. It is evaporated to dryness and the residue redissolved in 100 cm$^3$ of ethyl acetate; the solution is washed with saturated sodium chloride solution, dried over magnesium sulfate and evaporated. The N-[(S)-3-benzyloxycarbonylamino-4-phenyl-2-oxobutyl] -(S) Lys (Z)-OtBu is purified by chromatography on silica gel (solvent: CH$_2$Cl$_2$/MeOH 95:5) and dissolved in 50 cm$^3$ of a 2N solution of hydrochloric acid in ethyl acetate. After 18 hours at 20° C., the mixture is evaporated to dryness and the N-[(S)-3-benzyloxycarbonyl-amino-4-phenyl-2-oxobutyl]-(S) Lys (Z)-OH solidified in ether in the form of a hydrochloride and used without further treatment in the following stage.

STAGE C

N-[(S)-3-Benzyloxycarbonylamino-4-phenyl-2-oxobutyl]-(S) Lys (Z)-(S) ABO-(S) Arg (NO$_2$)-OCH$_2$C$_6$H$_5$ By replacing (2S, 3R) AHPA-(S) Lys (Z)-OH in Example 5 by N-[(S)-3-benzyloxycarbonylamino-4-phenyl2-oxobutyl]-(S) Lys (Z) OH, obtained in the preceding stage, N-[(S)-3-benzyloxycarbonylamino-4-phenyl-2-oxobutyl]-(S) Lys (Z)-(S) ABO-(S) Arg (NO$_2$)-OCH$_2$C$_6$H$_5$ is obtained, and this is purified by chromatography on silica gel (solvent: CH$_2$Cl$_2$/MeOH 90:10, Rf.: 0.65).

STAGE D

{(2S, 3S)-2-Hydroxy-3-[(Z)-amino]-4-phenylbutyl}-(S) Lys (Z)-(S) ABO-(S) Arg (NO$_2$)-OCH$_2$C$_6$H$_5$ (α isomer) and {(2R, 3S)-2-Hydroxy-3-[(Z)-amino]-4-phenylbutyl}-(S) Lys (Z)-(S) ABO-(S) Arg (NO$_2$)-OCH$_2$C$_6$H$_5$ (β isomer)

The keto group of N-[(S)-3-benzyloxycarbonylamino4-phenyl-2-oxobutyl]-(S) Lys (Z)-(S) ABO-(S) Arg (NO$_2$)-OCH$_2$C$_6$H$_5$, obtained in the preceding stage, is reduced to alcohol by the action of sodium borohydride in methanol. The two diastereoisomers are separated by chromatography on silica gel (solvent: CH₂Cl₂/ethanol 90:10).

STAGE E

[(2S, 3S)-2-Hydroxy-3-amino-4-phenyl-butyl]-(S) Lys-(S) ABO-(S) Arg-OH (α isomer) and [(2R, 3S)-2-Hydroxy-3-amino-4-phenyl-butyl]-(S) Lys-(S) ABO-(S) Arg-OH (β isomer)

Each of the isomers obtained in the preceding stage is treated according to the technique used in Example 1, Stage F, to give:

EXAMPLE 11

[(2S, 3S)-2-Hydroxy-3-amino-4-phenyl-butyl]-(S) Lys-(S) ABO-(S) Arg-OH (α isomer), which is lyophilized in the form of a triacetate.

EXAMPLE 12

[(2R, 3S)-2-Hydroxy-3-amino-4-phenyl-butyl]-(S) Lys-(S) ABO-(S) Arg-OH (β isomer), which is lyophilized in the form of a triacetate.
Mass spectrometry: (DCI spectrum (NH₃))
For both isomers:

| | |
|---|---|
| M/Z: | 585: $[M + H - H_2O]^+$ |
| | 543: $[M + H - H_2O - HN = . = NH]^+$ |

EXAMPLE 13 AND 14:

[(2S, 3R)-2-Hydroxy-3-amino-4-phenylbutyl]-(S) Lys-(S) ABO-(S) Arg-OH (α isomer) and [(2R, 3R)-2-Hydroxy-3-amino-4-phenylbutyl]-(S) Lys-(S) ABO-(S) Arg-OH (β isomer)

By replacing Z-(S)-phenylalanine by Z-(R)-phenylalanine in the procedure of Examples 11 and 12, the following are obtained successively:
(R)-3-Benzyloxycarbonylamino-4-phenyl-2-oxo-1-bromobutane
N-[(R)-3-Benzyloxycarbonylamino-4-phenyl-2-oxobutyl]-(S) Lys (Z)-OH
N-[(R)-3-Benzyloxycarbonylamino-4-phenyl-2-oxo-butyl]-(S) Lys (Z)-(S) ABO-(S) Arg (NO₂) OCH₂C₆H₅
then
{(2S, 3R)-2-Hydroxy-3-[(Z)-amino]-4-phenylbutyl}-(S) Lys (Z)-(S) ABO-(S) Arg (NO₂) OCH₂ C₆H₅ (α isomer)
and
{(2R, 3R)-2-Hydroxy-3-[(Z)-amino]-4-phenylbutyl}-(S) Lys-(S) ABO-(S) Arg (NO₂) OCH₂C₆H₅ (β isomer)
and then

EXAMPLE 13

[(2S, 3R)-2-Hydroxy-3-amino-4-phenylbutyl]-(S) Lys-(S) ABO-(S) Arg OH (α isomer), which is lyophilized in the form of a triacetate.

EXAMPLE 14

(2R,3R)-2-Hydroxy-3-amino-4-phenylbutyl]-(S) Lys-(S) ABO-(S) Arg-OH (β isomer), which is lyophilized in the form of a triacetate.

EXAMPLES 15 to 24

By the procedure used in Example 1, but replacing tBoc(S)PHI OH in Stage A by:
1-t-butoxycarbonyl-2-carboxindoline or tBoc(S)IND-OH (Example 15)
2-t-Butoxycarbonyl-1-carboxyisoindoline or tBoc(-S)ISI-OH (Example 16)
2-t-butoxycarbonyl-2-aza-3-carboxybicyclo[2.2.1]heptane or tBoc (S)ABH-OH (Example 17)
2-t-Butoxycarbonyl-3-carboxy-1,2,3,4-tetrahydrobeta-carboline or tBoc-(S) THC-OH (Example 18)
2-t-Butoxycarbonyl-1-carboxyperhydroisoindole or tBoc-PHII-OH (Example 19)
1-t-Butoxycarbonyl-2-carboxyperhydroquinoline or tBoc-PHQ-OH (Example 20)
2-t-Butoxycarbonyl-3-carboxyperhydroisoquinoline or tBoc-PHIQ-OH (Example 21)
1-t-Butoxycarbonyl-2-carboxyperhydrocyclopenta[b]pyrrole or tBoc-PCP-OH (Example 22)
1-t-Butoxycarbonyl-2-carboxy-1,2,3,4-tetrahydroquinoline or tBoc THQ-OH (Example 23)
2-t-Butoxycarbonyl-3-carboxy-1,2,3,4-tetrahydroisoquinoline or tBoc (S)THIQ-OH (Example 24),
the following are obtained, respectively:

EXAMPLE 15

(2S, 3R) AHPA-(S) Lys-(S) IND-(S) Arg-OH, which is lyophilized in the form of a diacetate.

EXAMPLE 16

(2S, 3R) AHPA-(S) Lys-(S) ISI-(S) Arg-OH, which is lyophilized in the form of a diacetate.

EXAMPLE 17

(2S, 3R) AHPA-(S) Lys-(S) ABH-(S) Arg-OH, which is lyophilized in the form of a diacetate.

EXAMPLE 18

(2S, 3R) AHPA-(S) Lys-(S) THC-(S) Arg-OH, which is lyophilized in the form of a diacetate.

EXAMPLE 19

(2S, 3R) AHPA-(S) Lys 0 PHII-(S) Arg-OH, which is lyophilized in the form of a diacetate.

EXAMPLE 20

(2S, 3R) AHPA-(S) Lys-PHQ-(S) Arg-OH, which is lyophilized in the form of a diacetate.

EXAMPLE 21

(2S, 3R) AHPA-(S) Lys-PHIQ-(S) Arg-OH, which is lyophilized in the form of a diacetate.

EXAMPLE 22

(2S, 3R) AHPA-(S) Lys-PCP-(S) Arg-OH, which is lyophilized in the form of a diacetate.

EXAMPLE 23

(2S, 3R) AHPA-(S) Lys-THQ-(S) Arg-OH, which is lyophilized in the form of a diacetate.

EXAMPLE 24

(2S, 3R) AHPA-(S) Lys-(S) THIQ-(S) Arg-OH, which is lyophilized in the form of a diacetate.

PHARMACOLOGICAL STUDY OF THE COMPOUNDS OF THE INVENTION

The capacity of the compounds of the invention to stimulate the activity of immunocompetent cells was verified in vitro and in vivo.

EXAMPLE 25

Stimulation of phagocytosis in vitro

In vitro, the technique described by DESCAMPS B., 1980 (Ann. Immunol. Inst. Past., 131 C, No. 2, p. 10) was used in order to measure the stimulation of the phagocytic capacity of macrophages by the compounds of the invention: mouse (strain $B_6D_2F_1$) peritoneal macrophages were inoculated into Petri dishes in the proportion of $10^4$ cells per dish. After attachment of the culture to the medium, the compounds of the invention were added in aqueous solution at a concentration of 25 micromolar per dish, and sheep red cells opsonized with specific immunoglobulins were then introduced. After 1 hour of contact, the cultures were washed and the number of macrophages which had ingested more than 2 red cells was counted.

The compounds of the invention increase by approximately 25% the phagocytic power of macrophages, relative to control cultures. Under the same conditions, the activation power of tuftsin is 15%.

EXAMPLE 26

Promotion of NK activity

The compounds according to the invention were also tested for their capacity to promote "natural killer" activity. Cells endowed with this capacity form the body's first line of defense with respect to septic, viral or tumor invasion.

In order to assess their stimulatory power, compounds according to the invention were studied according to the technique of REYNOLDS et al. 1981 (J. Immunol. 127, 282).

The compounds were injected intravenously at a dose of 20 to 50 μg/kg into $B_6D_2F_1$ strain mice.

Three days after the treatment, the animals were sacrificed and their spleen was removed and disintegrated into its constituent cells, which were inoculated in culture in the presence of YAC-1 tumor cells previously labelled with radioactive chromium. After incubation, the destructive power of the compounds of the invention was measured by the quantity of chromium released.

At a dose of 25 μg/kg, the compounds of the invention induce an increase in the release of chromium which is of the order of 15% relative to the control, whereas tuftsin at a dose of 40 μg/kg produces a release of only 10%.

EXAMPLE 27

Inhibition of growth of B 16 melanoma

Melanomas of cancerous tumors which are sensitive to the reaction of the patient's immune system. They hence represent a model of choice for assessing any stimulation of antitumor defense.

The compounds of the invention were shown to be capable of reducing by 40% the rate of growth of mouse B 16 melanoma, when the products are administered intraperitoneally in the proportion of 20 μg/kg 3 times per week. Under the same conditions, tuftsin was shown to be incapable of promoting a reduction in the growth of the grafted tumor.

EXAMPLE 28

Increase in the resistance of animals to infection

Some pathogenic bacterial strains are capable of killing the healthy host into which they have been inoculated. This is the case, for example, with *Klebsiella pneumoniae*, the agent responsible for pneumonia (Parant, M. et al., Proc. Natl. Acad. Sci. USA, 1978, 75, No. 7, 3395).

At a dose of 60 μg per animal, the compounds of the invention were capable of protecting against death by infection or female Swiss mice, weighing 20 to 25 g, into which *Klebsiella pneumoniae* strain 7823 was inoculated IP, when they were administered 48 hours before infection. Under the same conditions, tuftsin was capable of saving only 20% of the animals.

EXAMPLE 29

Increase in the lymphocyte response to mitogens

Lectins extracted from plants are capable of substituting in vitro for the stimulation of lymphocyte proliferation normally brought about by specific antigens. These agents are lymphocyte mitogens.

After lymphocytes are brought into contact with such a mitogen, it is possible to measure the intensity of the proliferation, and thereby to measure the immunoprotective reactivity of animals treated with a compound (Daguillar, F., Med. Clin. North. Am., 56, 293).

Thus, spleen lymphocytes of mice treated with 0.5 mg per kg of the compounds according to the invention, and exposed to concanavaline A at a concentration of 0.5 mg/ml, respond by a proliferation approximately equal to 1.8-fold that of lymphocytes of untreated animals.

EXAMPLE 30

Pharmaceutical compositions Injectable solution

| | |
|---|---|
| (2S, 3R) AHPA - (S) Lys - (S) PHI - (S) Arg OH | 0.020 g |
| Water for injections qs | 1.5 cm³ |
| Tablet | |
| Manufacturing formula for 1,000 tablets: | |
| (2S, 3R) AHPA - (S) Lys - (S) PHI - (S) Arg OH | 25 g |
| Hydroxypropyl cellulose | 1 g |
| Corn starch | 10 g |
| Lactose | 100 g |
| Magnesium stearate | 2 g |
| Talc | 2 g |

We claim:

1. A compound selected from those of the formula:

$$R-\underset{Y}{\underset{|}{CH}}-\underset{X}{\underset{\|}{C}}-Lys-N\underset{A}{\overbrace{\phantom{XXX}}}CH-CO-Arg-OH \quad (I)$$

in which:

X denotes either an oxygen atom, or two hydrogen atoms;

Y denotes either a hydrogen atom, or a hydroxyl group;

or

Y denotes an amino group on condition that X denotes two hydrogen atoms;

R denotes a hydrogen atom, or a straight- or branched-chain alkyl group having 1 to 6 carbon atoms, optionally substituted with one or more hydroxy, amino, mercapto, methylthio or carboxy groups, or an aryl group;

Lys and Arg denote, respectively, lysyl and arginyl residues engaged in peptide bonds,

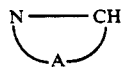

denotes a bicyclic structure selected from the group consisting of indoline, isoindoline, tetrahydroquinoline, tetrahydroisoquinoline, perhydroindole, perhydroisoindole, perhydroquinoline, perhydroisoquinoline, perhydrocyclopenta[b]pyrrole, 2-azabicyclo[2.2.2]octane, and 2-azabicyclo-[2.2.1]heptane; their enantiomers, epimers and diastereoisomers, as well as their addition salts with a pharmaceutically-acceptable acid or base.

2. A compound as claimed in claim 1 in which the cyclic structure

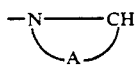

denotes perhydroindole or 2-azabicyclo[2.2.2]octane, their enantiomers, epimers and diastereoisomers, as well as their addition salts with a pharmaceutically acceptable acid or base.

3. Compound of claim 1 being AHPA-(S) Lys-(S) PHI-(S) Arg-OH, its isomers or its addition salt with a pharmaceutically acceptable acid or base.

4. Compound of claim 1 being (2S, 3R) AHPA-(S) Lys-(S) PHI-(S) Arg-OH or its addition salt with a pharmaceutically acceptable acid or base.

5. Compound of claim 1 being AHPA-(S) Lys-(S) ABO-(S) Arg-OH, its isomers or its addition salt with a pharmaceutically acceptable acid or base.

6. Compound of claim 1 being N-[(R)-2-Hydroxy-3-aminobutyryl]-(S) Lys-(S) ABO-(S) Arg-OH, its isomers and or its addition salt with a pharmaceutically acceptable acid or base.

7. Compound of claim 1 being [(S)-3-Phenyl-2-aminopropyl]-(S) Lys-(S) ABO-(S) Arg-OH, its isomers and its addition salt with a pharmaceutically acceptable acid or base.

8. Compound of claim 1 being [(S)-2-Hydroxy-3-amino-4-phenylbutyl]-(S) Lys-(S) ABO-(S) Arg-OH, its isomers or its addition salt with a pharmaceutically acceptable acid or base.

9. Compound of claim 1 being [(R)-2-Hydroxy-3-amino-4-phenylbutyl]-(S) Lys-(S) ABO-(S) Arg-OH, its isomers or its addition salt with a pharmaceutically acceptable acid or base.

10. A compound of claim 1, wherein the aryl group within the scope of "R" is selected from the group consisting of phenyl, pyrridyl, and thienyl groups.

11. A pharmaceutical composition useful in the treatment of a infectious condition susceptible thereto, comprising, as active principle, an effective amount of a compound of claim 1 in combination with a pharmaceutically-acceptable vehicle or excipient.

12. A pharmaceutical composition of claim 11 in injectable form.

13. A method for treating a living animal body afflicted with an infectious condition susceptible thereto, comprising the step of administering to the said living animal an amount of a compound of claim 1 which is effective for alleviation of the said condition.

* * * * *

UNITED STATES PATENT AND TRADEMARK OFFICE
CERTIFICATE OF CORRECTION

PATENT NO. : 5,047,400

DATED : Sep. 10, 1991

INVENTOR(S) : Michel Vincent, Georges Remond, Bernard Portevin, Claude Cudennec

It is certified that error appears in the above-identified patent and that said Letters Patent is hereby corrected as shown below:

Column 6, approximately line 44; "($NO_2OCH_2$" should read -- ($NO_2$)$OCH_2$ --.

Column 8, line 48; delete the line; "Mass spectrometry; (DCI spectrum: ($NH_3$))".

Column 9, line 7; "(2S,b 3R)" should read -- (2S, 3R) --.

Column 9, line 17; "$H_5$The" should read -- $H_5$. The --.

Column 9, line 19; "mix-ture" should read -- mixture --.

Column 9, approximately line 48; "chromatograohy:" should read -- chromatography: --.

Column 11, line 14; [(Z)amino] should read --[(Z)-amino] --.

Column 11, line 31; "S) Lys" should read -- (S) Lys --.

Column 11, line 69; "p 109" should read -- p. 109 --.

Column 12, line 26; "phenyl2" should read -- phenyl-2 --.

Column 12, line 53; "phenyl2" should read -- phenyl-2 --

Column 12, line 68; "bonylamino4" should read --bonylamino-4 --.

Column 14, line 7/8; move the opening parenthesis "(" from line 8 and insert at the beginning of line 9 before "S".

Column 14, line 20/21; move the closing bracket to the preceding line and insert inside the hyphen.

Column 16, line 41; "move "Injectable solution" down one line and insert at the left hand margin of Column 16.

UNITED STATES PATENT AND TRADEMARK OFFICE
CERTIFICATE OF CORRECTION

PATENT NO. : 5,047,400

DATED : Sep. 10, 1991

INVENTOR(S) : Michel Vincent, Georges Remond, Bernard Portevin, Claude Cudennec It is certified that error appears in the above-identified patent and that said Letters Patent is hereby corrected as shown below:

Column 18, line 2; "PHI-(5)" should read -- PHI - (S) --.(old Cl.15)

Column 18, line 9; "mers and or" should read -- mers or --. (R&A 2-12-91, Pg. 2) (old Cl. 7)

Column 18, line 12; "and" should read -- or --. (R&A 2-12-91,P.2, old Cl. 8)

Column 18, line 27; "a infectious" should read -- an infectious --. (Exmnr Amdt 3-12-91 - old Cl. 16)

Signed and Sealed this

Sixteenth Day of March, 1993

*Attest:*

STEPHEN G. KUNIN

*Attesting Officer*  Acting Commissioner of Patents and Trademarks